United States Patent [19]

Sato et al.

[11] Patent Number: 4,835,290

[45] Date of Patent: May 30, 1989

[54] PROCESS FOR PREPARING 13-HYDROXY-5-KETOMIBEMYCIN DERIVATIVES HAVING ACARICIDAL, INSECTICIDAL AND ANTHELMINTIC ACTIVITY

[75] Inventors: Kazuo Sato; Takao Kinoto; Shigeru Mio; Toshiaki Yanai, all of Tokyo, Japan

[73] Assignee: Sankyo Company, Limited, Tokyo, Japan

[21] Appl. No.: 115,642

[22] Filed: Oct. 26, 1987

Related U.S. Application Data

[63] Continuation of Ser. No. 790,748, Oct. 24, 1985, abandoned.

[30] Foreign Application Priority Data

Oct. 26, 1984 [JP] Japan ............................. 59-225551
Apr. 2, 1985 [JP] Japan ............................. 60-69804

[51] Int. Cl.$^4$ ........................................... C07D 407/14
[52] U.S. Cl. .................................................. 549/264
[58] Field of Search ....................................... 549/264

[56] References Cited

U.S. PATENT DOCUMENTS

| | | | |
|---|---|---|---|
| 4,134,973 | 1/1979 | Fisher et al. | 536/7.1 |
| 4,142,056 | 2/1979 | Sih | 560/121 |
| 4,169,940 | 10/1979 | Dolak | 536/13 |
| 4,346,171 | 8/1982 | Takiguchi et al. | 514/451 |
| 4,423,209 | 12/1983 | Mrozik | 549/264 |

FOREIGN PATENT DOCUMENTS

033289 2/1984 Japan .

OTHER PUBLICATIONS

Bulletin of the Chemical Society of Japan, vol. 42, 2056–2058 (1969) K. Javaid et al. "Selenium Dioxide Oxidation of Styrene and Norbornene".

J. Org. Chem., vol. 33, No. 7, Jul. 1968, J. Schaefer et al. "Selenium Dioxide Oxidations, III, The Oxidation of Olefins.".

*Primary Examiner*—Jane T. Fan
*Attorney, Agent, or Firm*—Frishauf, Holtz, Goodman & Woodward

[57] ABSTRACT

13-Hydroxy-5-ketomilbemycin derivatives are prepared by oxidizing a 5-ketomilbemycin with selenium dioxide in the presence of a lower aliphatic carboxylic acic. A range of new 13-acyloxy-5-ketomilbemycins and a method or preparing them are also disclosed. These compounds have acaricidal, insecticidal and authelmintic activities.

30 Claims, No Drawings

PROCESS FOR PREPARING 13-HYDROXY-5-KETOMIBEMYCIN DERIVATIVES HAVING ACARICIDAL, INSECTICIDAL AND ANTHELMINTIC ACTIVITY

This application is a continuation, of application Ser. No. 790,748, filed Oct. 24, 1985 now abandoned.

BACKGROUND OF THE INVENTION

The present invention relates to a process for preparing certain 13-hydroxy-5-ketomilbemycin derivatives, which are useful as intermediates in the preparation of therapeutically useful milbemycin derivatives, and provides certain novel 13-substituted-5-ketomilbemycin derivatives which can be involved in that preparation.

A series of 13-hydroxy-5-ketomilbemycin derivatives is disclosed in U.S. Pat. No. 4,423,209 and such compounds constitute important intermediates in the synthesis of other milbemycin derivatives which have valuable acaricidal, insecticidal and anthelmintic activities.

The process for preparing a 13-hydroxy-5-ketomilbemycin disclosed in this U.S. patent comprises treating a 13-hydroxy-5-methoxymilbemycin with mercuric acetate to give an enol ether, and then treating this enol ether with an acid. Such a process works efficiently and highly satisfactorily on a laboratory scale, but it has recently become apparent that certain disadvantages inherent in this process may make it difficult to carry out the process economically on the large scale required for industrial production. For example, the availability of the starting material for this process is limited, the reaction conditions required (notably the temperature) are inconvenient and the yields tend to be a little low. Moreover, since a highly poisonous mercuric compound is employed in the process, care needs to be taken to avoid pollution of the environment and poisioning of factory workers. These practical problems all add to the cost of industrial scale production and, exacerbated by the low yields, suggest that the prior art process may not be satisfactory for the large scale production of 13-hydroxy-5-ketomilbemycins.

We have now discovered a process for preparing these compounds which overcomes many of the disadvantages of the prior art process and which notably enables the products to be produced in significantly higher yields: on a laboratory scale, yields in the region of 50% have generally been achieved. It is believed that these factors will enable the process of the invention to be carried out more economically on an industrial scale than can the prior art process. In the course of developing the process of the invention, a certain new class of milbemycin derivatives has been discovered.

BRIEF SUMMARY OF THE INVENTION

It is, accordingly, an object of the present invention to provide a process for producing 13-hydroxy-5-ketomilbemycins.

It is a further, and more specific, object of the invention to provide such a process which enables the 13-hydroxy-5-ketomilbemycins to be produced in higher yields.

It is a still further object of the invention to provide a series of 13-substituted-5-ketomilbemycin derivatives as new compounds.

The process of the present invention prepares compounds of formula (I):

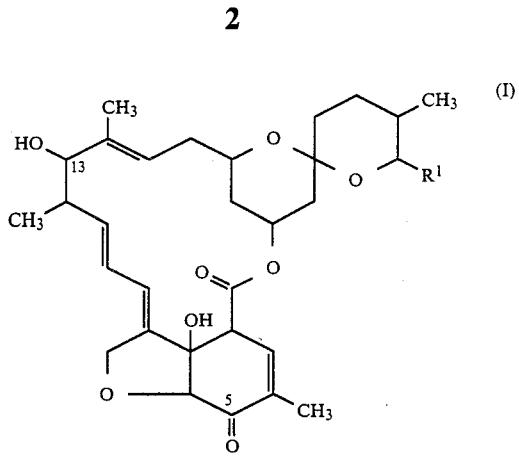

(in which $R^1$ represents a methyl, ethyl, isopropyl or sec-butyl group) by treating a compound of formula (III):

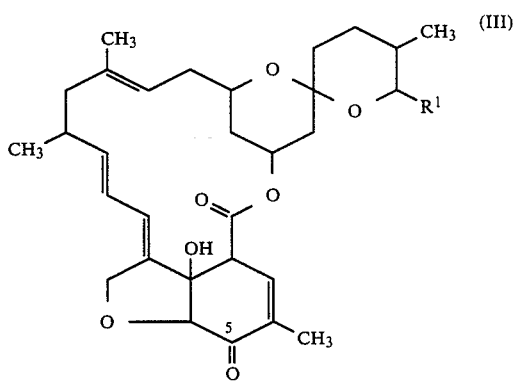

(wherein $R^1$ is as defined above) with selenium dioxide in the presence of a carboxylic acid of formula (IV):

$R^2$—COOH (IV)

(wherein $R^2$ represents a hydrogen atom or a $C_1$-$C_4$ alkyl group) to give either said compound of formula (I) or a compound of formula (II):

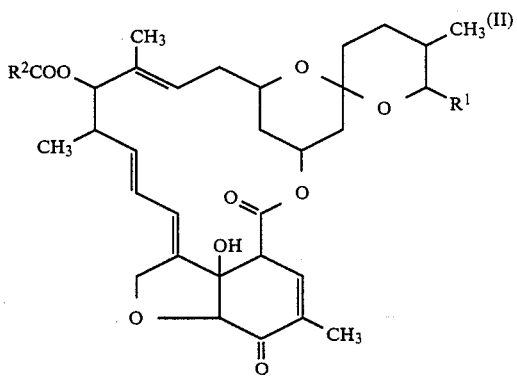

(wherein $R^1$ and $R^2$ are as defined above) and, if necessary, hydrolizing said compound of formula (II).

The invention also provides, as new compounds, compounds of formula (V):

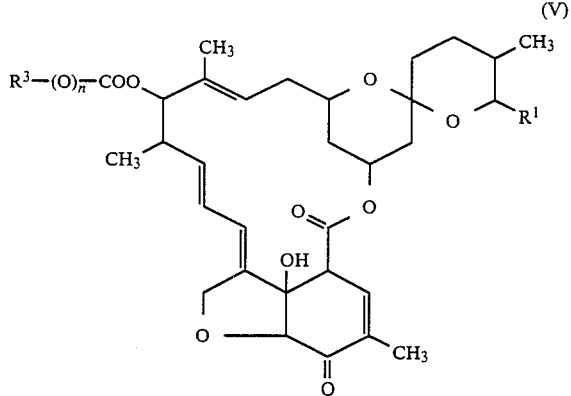

(V)

wherein:
R¹ is as defined above;
n is the cypher 0 or the integer 1; and
R³ represents a hydrogen atom, a $C_1$-$C_{18}$ alkyl group, a $C_3$-$C_{10}$ cycloalkyl group, a $C_7$-$C_9$ aralkyl group, a $C_2$-$C_6$ alkenyl group, a $C_2$-$C_6$ alkynyl group, a $C_5$-$C_{10}$ cycloalkenyl group, a $C_6$-$C_{10}$ carbocyclic aryl group or a heterocyclic group having from 5 to 14 ring atoms of which from 1 to 5 are hetero-atoms selected from the group consisting of oxygen, sulfur and nitrogen atoms, or said alkyl, alkenyl or alkynyl group having at least one substituent selected from the group consisting of substituents (a), or said cycloalkyl, cycloalkenyl, aralkyl, aryl or heterocyclic group having at least one substituent selected from the group consisting of substituents (a) and (b):

substituents (a): $C_1$-$C_6$ alkoxy groups, $C_2$-$C_7$ alkoxycarbonyl groups, halogen atoms, hydroxy groups, carboxy groups, amino groups, $C_1$-$C_6$ alkylamino groups, dialkylamino groups where each alkyl part is $C_1$-$C_6$, carboxylic acylamino groups, cyano groups, carbamoyl groups, alkylcarbamoyl groups where the alkyl part is $C_1$-$C_6$, dialkylcarbamoyl groups where each alkyl part is $C_1$-$C_6$, mercapto groups, $C_1$-$C_6$ alkylthio groups, $C_1$-$C_6$ alkylsulfinyl groups, $C_1$-$C_6$ alkylsulfonyl groups, nitro groups, phenoxy groups, phenoxy groups having from 1 to 5 halogen substituents and heterocyclic groups having 5 or 6 ring atoms of which from 1 to 3 are hetero-atoms selected from the group consisting of nitrogen, oxygen and sulfur atoms, said heterocyclic groups being unsubstituted or having at least one substituent selected from the group consisting of substituents (a) and (b); and substituents (b): $C_1$-$C_6$ alkyl groups, $C_2$-$C_6$ alkenyl groups, $C_2$-$C_6$ alkenyl groups having at least one halogen substituent, alkoxyalkyl groups where both the alkoxy and the alkyl parts are $C_1$-$C_6$ and $C_1$-$C_6$ alkyl groups having at least one halogen substituent.

The invention also provides a process for preparing said compounds of formula (V), which comprises reacting a compound of formula (I), defined above, with a compound of formula (VI):

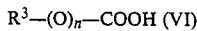

R³—(O)_n—COOH (VI)

(wherein R³ and n are as defined above) or with a reactive derivative thereof.

In the course of preparing compounds of formula (I), employing compounds of formula (IV) in which R² represents a hydrogen atom or a methyl group, compounds of formula (II) may be prepared as intermediates and these, of course, are identical with those compounds of formula (V) in which n is the cypher 0 and R³ represents a hydrogen atom or a methyl group.

DETAILED DESCRIPTION OF INVENTION

The compounds of, and employed in, the present invention are milbemycin derivatives and, as such, are named as derivatives of the various milbemycins. Thus, those compounds where R¹ represents a methyl group are named as derivatives of milbemycin A₃, those compounds where R¹ represents an ethyl group are named as derivatives of milbemycin A₄, and those compounds where R¹ represents an isopropyl group are named as derivatives of milbemycin D. A fuller discussion of the history and naming of the milbemycin compounds appears in U.S. Pat. No. 4,346,171, the disclosure of which is incorporated herein by reference.

In the compounds of formulae (I)–(VI), where R² or R³ represents a $C_1$-$C_4$ alkyl group, this may be a straight or branched chain alkyl group for example a methyl, ethyl, propyl, isopropyl, butyl, isobutyl, sec-butyl or t-butyl group. Where R³ in the compounds of formulae (V) and (VI) represents a $C_1$-$C_{18}$ alkyl group, this likewise may be a straight or branched chain group and examples include those $C_1$-$C_4$ alkyl groups mentioned above as well as the pentyl, isopentyl, neopentyl, t-pentyl, hexyl, isohexyl, 1-ethylbutyl, heptyl, octyl, isooctyl, 2-ethylhexyl, nonyl, decyl, isodecyl, undecyl, dodecyl, tetradecyl, hexadecyl and octadecyl groups.

Where R³ represents a cycloalkyl group, this has from 3 to 10, preferably from 3 to 7, ring carbon atoms and maybe a monocyclic or polycyclic, preferably bicyclic, group; examples of such groups include the cyclopropyl, cyclobutyl, cyclopentyl, cyclohexyl and bicyclo[2.2.1]heptyl groups.

Where R³ represents a cycloalkenyl group having from 5 to 10 ring atoms, it may be any one of the cycloalkyl groups listed above but having at least one unsaturated carbon-carbon bond in the ring. Examples include the cyclopentenyl, cyclohexenyl, cycloheptenyl, cyclooctenyl, tetrahydronaphthyl and octahydronaphthyl groups, of which the cyclohexenyl, especially 1-cyclohexenyl, groups are preferred.

Where R³ represents an aralkyl group having from 7 to 9 carbon atoms, it is preferably a $C_1$-$C_3$ alkyl group having a phenyl substitutent, for example a benzyl, α-methylbenzyl, α,α-dimethylbenzyl, phenethyl or 3-phenylpropyl group.

Where R³ represents an alkenyl or alkynyl group having from 2 to 6 carbon atoms, it is more preferably such a group having from 2 to 4 carbon atoms and having 1 or 2 unsaturated carbon-carbon double or triple bonds, for example the vinyl, propenyl (e.g. allyl), isopropenyl, butenyl, butadienyl, methallyl, hexadienyl, ethynyl or propynyl groups.

Where R³ represents a carbocyclic aryl group having from 6 to 10 carbon atoms, it is preferably a phenyl or naphthyl (1- or 2-naphthyl) group.

Where R³ represents a heterocyclic group, this contains from 5 to 10 ring atoms, of which at least one, preferably from 1 to 5 and ore preferably from 1 to 3, are hetero-atoms selected from the group consisting of nitrogen, oxygen and sulfur atoms. The atoms of the heterocyclic group may be fully saturated or they may be unsaturated and, if unsaturated, they may be aromatic in character. Examples of such groups include the furyl, thienyl, pyrrolyl, pyridyl, thiazolyl, isothiazolyl, oxazolyl, isooxazolyl, imidazolyl, pyrazolyl, pyranyl, pyrazinyl, pyridazinyl, pyrimidinyl, benzofuranyl, benzothienyl, indolyl, quinolyl, isoquinolyl, quinazolinyl, quinoxalinyl, naphthyridinyl and xanthenyl groups, and their partly or fully saturated analogs, for example the tetrahydrofuranyl, tetrahydrothienyl, pyrrolidinyl, thiazolidinyl, imidazolidinyl, imidazolinyl, oxazolinyl, pyrazolidinyl, piperazinyl, tetrahydropyrimidinyl, dihydropyridazinyl, morpholinyl, indolinyl and tetrahydroquinolyl groups.

Any of the groups defined above and represented by $R^3$ can be unsubstituted or they can have one or more substituents. There is no general limitation upon the number of substituents which any group may bear, although there may, in any individual case, be practical limitations upon the maximum number of such substituents. Thus, in all cases, the maximum number of substituents which any group may bear is determined by the number of substitutable positions on that group and hence groups with more atoms can, in general, bear more substituents. Also, the number of substituents may be limited by steric considerations. For example, where the group to be substituted is relatively small and the substituent is relatively bulky, the number of substituents which can, in practice, be accommodated may be less than the theoretical maximum. Such matters are, however, well-known to those skilled in the art and require no further discussion or definition here.

Where the substituent is an alkyl group, it may be a straight or branched chain alkyl group having from 1 to 6 carbon atoms and examples include the methyl, ethyl, propyl, isopropyl, butyl, isobutyl, sec-butyl, t-butyl, pentyl and hexyl groups.

Where the substituent is an alkoxy group, it may likewise be a straight or branched chain group having from 1 to 6 carbon atoms and examples include the methoxy, ethoxy, propoxy, isopropoxy, butoxy, isobutoxy, t-butoxy, pentyloxy and hexyloxy groups.

Where the substituent is an alkoxyalkyl group, both the alkoxy part and the alkyl part may be straight or branched chain groups and each has from 1 to 6 carbon atoms; examples of the alkoxy and alkyl parts are included within the alkyl and alkoxy groups defined above. More preferably, the alkoxyalkyl group has a total of up to 6 carbon atoms and preferred examples of such groups include the methoxymethyl, ethoxymethyl, propoxymethyl, butoxymethyl, 2-methoxyethyl, 2-ethoxyethyl, 2-butoxyethyl and 3-propoxypropyl groups.

Where the substituent is an alkoxycarbonyl group, it has a total of from 2 to 7, preferably from 2 to 5, carbon atoms and the alkoxy part may be any one of those alkoxy groups described above. Preferred examples of such alkoxycarbonyl groups include the methoxycarbonyl, ethoxycarbonyl, propoxycarbonyl, butoxycarbonyl and t-butoxycarbonyl groups.

Where the substituent is a haloalkyl group, it has from 1 to 6, preferably from 1 to 3, carbon atoms and may be a straight or branched chain group, including halogenated analogs of the $C_1-C_6$ alkyl groups described above. The number of halogen atoms may range from a minimum of 1 to a maximum of complete halogenation (i.e. a perhaloalkyl group), although, in practice, groups with from 1 to 3 halogen atoms are generally most conveniently available. Examples of such haloalkyl groups include the chloromethyl, bromomethyl, iodomethyl, fluoromethyl, dichloromethyl, trifluoromethyl, 2-chloroethyl, 2,2,2-trichloroethyl, 2-bromopropyl and 2,3-dibromopropyl groups.

Where the substituent is an alkenyl group having from 2 to 6 carbon atoms, it may be a straight or branched chain group, for example a vinyl, propenyl (e.g. allyl), isopropenyl, butenyl, butadienyl, methallyl or hexadienyl group.

Where the substituent is an alkenyl group having at least one halogen (e.g. fluorine, chlorine, bromine or iodine, preferably chlorine) substituent, it may be a halogenated analog of any of the alkenyl groups listed above, ranging from a monohalo to a perhalo (preferably trihalo) compound. Preferred haloalkenyl groups are 2-chlorovinyl, 2,2-dichlorovinyl, 3-chloroallyl, 2,2-difluorovinyl and 1,2,2-trichlorovinyl groups.

Where the substituent is a halogen atom, it is preferably a chlorine, bromine, fluorine or iodine atom.

Where the substituent is a mono- or di-alkylamino group, the or each alkyl part is $C_1-C_6$, preferably $C_1-C_4$, alkyl and examples are the alkyl groups given above. Preferred such alkylamino groups include the methylamino, ethylamino, propylamino, isopropylamino, dimethylamino, diethylamino, methyl(ethyl)amino and methyl(butyl)amino groups.

Where the substituent is a carboxylic acylamino group, the carboxylic acyl part may be an aromatic, aliphatic, cycloaliphatic or heterocyclic acyl group in which the aromatic, aliphatic, cycloaliphatic and heterocyclic parts are as defined above in relation to the aryl, alkyl, alkenyl, alkynyl, cycloalkyl and heterocyclic groups, respectively. However, it is most preferably a $C_1-C_7$, more preferably $C_2-C_5$, alkanoylamino group, for examle the acetylamino, propionylamino or butyrylamino groups.

Where the substituent is a mono- or di-alkylcarbamoyl group, the or each alkyl part is a $C_1-C_6$, preferably $C_1-C_4$, alkyl group, examples of which are as given above. Preferred examples of such alkylcarbamoyl groups include the methylcarbamoyl, ethylcarbamoyl, butylcarbamoyl and dimethylcarbamoyl groups.

Where the substituent is an alkylthio group, it may be a straight or branched chain group having from 1 to 6, more preferably from 1 to 4, carbon atoms and the alkyl part may be any one of those alkyl groups defined above. Preferred examples of such alkylthio groups include the methylthio, ethylthio, propylthio, butylthio and sec-butylthio groups.

Where the substituent is an alkylsulfinyl group, the alkyl part may be a straight or branched chain $C_1-C_6$, preferably $C_1-C_4$, alkyl group and may be any one of those alkyl groups exemplified above. Preferred examples of such alkylsulfinyl groups include the methylsulfinyl, ethylsulfinyl, propylsulfinyl and butylsulfinyl groups.

Where the substituent is an alkylsulfonyl group, the alkyl part may be a straight or branched chain $C_1-C_6$, preferably $C_1-C_4$, alkyl group, for example any one of those alkyl groups exemplified above. Preferred examples of such alkylsulfonyl groups include the methanesulfonyl, ethanesulfonyl, propanesulfonyl and butanesulfonyl groups.

Where the substituent is a halogenated phenoxy group, this may have from 1 to 5, preferably from 1 to 3, halogen substituents, the halogen substituents being, for example, chlorine, bromine, iodine or fluorine atoms. Examples of such halogenated phenoxy groups include the chlorophenoxy, bromophenoxy, fluorophenoxy, iodopheoxy and dichlorophenoxy groups.

Where the substituent is a heterocyclic group having 5 or 6 ring atoms, of which from 1 to 3 are hetero-atoms selected from the group consisting of nitrogen, oxygen and sulfur atoms, it may be any one of those 5- and 6-membered heterocyclic groups exemplified above in relation to the heterocyclic group which may be represented by $R^3$, or a 2,2-dimethyl-1,3-dioxolanyl group.

Preferred examples of groups which may be represented by $R^3$ include: the methyl, ethyl, isopropyl, butyl, t-butyl, pentyl, octyl, trifluoromethyl, 2-chloroethyl, 2,2,2-trichloroethyl, 2,2,2-trifluoroethyl, 1-chloropropyl, methoxymethyl, 2-methoxyethyl, 2-ethoxyethyl, phenoxymethyl, 4-fluorophenoxymethyl, 2-hydroxyethyl, 2-mercaptoethyl, 2-carboxyethyl, cyclopropyl, 2-(2,2-dichlorovinyl)-3,3-dimethylcyclopropyl, cyclobutyl, 2-furfuryl, 2-thenyl, 2,2-dimethyl-1,3-dioxolan-4-ylmethyl, 2,2-dichlorovinyl, 1,2,2-trichlorovinyl, 2,2-difluorovinyl, 1-propenyl, allyl, isopropenyl, 1-butenyl, 2-butenyl, 2-methylallyl, ethynyl, 2-propynyl, 1-cyclohexenyl, benzyl, phenyl, o-chlorophenyl, m-chlorophenyl, p-chlorophenyl, o-fluorophenyl, m-fluorophenyl, p-fluorophenyl, o-bromophenyl, m-bromophenyl, p-bromophenyl, p-methoxyphenyl, p-nitrophenyl, p-t-butylphenyl, o-trifluoromethylphenyl, m-trifluoromethylphenyl, 2-furyl, 3-furyl, 2-thieyl, 3-thienyl, 1-pyrrolyl, 2-pyrrolyl, 1-pyrrolidinyl, 2-pyridyl, 2-quinolinyl, 6-fluoro-2-pyridyl, 5-chloro-2-thienyl and 5-fluoro-2-furyl groups.

In the process of the present invention for preparing compounds of formulae (I) and (II), the known 5-ketomilbemycin derivative of formula (III) is reacted with selenium dioxide in the presence of a carboxylic acid of formula (IV):

$R^2$—COOH (IV)

(in which $R^2$ is as defined above).

The compounds of formula (III), which are the starting materials employed in this process, are known compounds and are described, for example, in U.S. Pat. No. 4,423,209 or in U.S. patent application Ser. No. 555,185 which issued as U.S. Pat. No. 4,547,520.

The process of the invention constitutes an oxidation process of the allyl-type configuration around the 13-position of the milbemycin molecule and is effected by treating the compound of formula (III) with selenium doxide in the presence of a carboxylic acid of formula (IV). Where $R^2$ in the carboxylic acid of formula (IV) is a $C_1$–$C_4$ alkyl group, it may be any one of the straight or branched chain $C_1$–$C_4$ alkyl groups exemplified above. The carboxylic acid of formula (IV) is preferably formic acid or acetic acid, more preferably formic acid, and, in these cases, the corresponding 13-acyloxy compound of formula (II) may be prepared in addition to the 13-hydroxy compound of formula (I). We prefer to employ at least one mole of the carboxylic acid of formula (IV) per mole of the 5-ketomilbemycin of formula (III), preferably more than one mole of said carboxylic acid (IV) per mole of 5-ketomilbemycin (III). The carboxylic acid of formula (IV) may be employed in significantly greater amounts, as it can then serve as the reaction solvent and this, indeed, is a preferred embodiment of the process of the present invention.

Where a solvent other than the carboxylic acid of formula (IV) is employed, the nature of such a solvent is not critical, provided that it has no adverse effect upon the reaction. Examples of such solvents include: hydrocarbons, preferably aliphatic or aromatic hydrocarbons, such as hexane or benzene; halohydrocarbons, preferably aliphatic halohydrocarbons, such as methylene chloride or chloroform; ethers, such as diethyl ether, tetrahydrofuran or dioxane; alcohols, such as methanol or ethanol; esters, such as ethyl acetate or pentyl acetate; amides, such as dimethylformamide or dimethylacetamide; dimethyl sulfoxide; water; and mixtures of any two or more of these solvents.

The amount of selenium dioxide is preferably from 1 to 10 moles, more preferably from 1 to 3 moles, per mole of the 5-ketomilbemycin of formula (III).

There is no particular limitation on the reaction temperature and the rection will take place over a wide range of temperatures. Normally we prefer to carry out the reaction at a temperature of from 0° to 80° C., more preferably at room temperature or with gentle heating. At such temperatures, the time required for the reaction will normally be within the range from 30 minutes to 1 day.

In general, this reaction of the 5-ketomilbemycin (III) with selenium dioxide and the carboxylic acid (IV) will produce a mixture of the 13-hydroxy-5-ketomilbemycin (I) and the 13-acyloxy-5-ketomilbemycin (II). The relative proportions of the compounds of formulae (I) and (II) produced by this reaction will vary very widely, depending upon the reaction conditions, particularly the type of carboxylic acid (IV) and the amount of selenium dioxide. For example, when the preferred carboxylic acid (IV), formic acid, is used, the corresponding 13-formyloxy-5-ketomilbemycin (II) will be produced in a relatively large proportion. With higher acids than acetic acid, relatively lower proportions of the 13-acyloxy compound (II) will be prepared.

These compounds of formula (II) are novel and have themselves a certain acaricidal activity. However, it is believed that they will be of more value for conversion to other compounds having greater acaricidal activity, as they have a reactive functional group (the acyl, e.g. formyl, group) at the 13-position.

Where the desired final product is the 13-hydroxy-5-ketomilbemycin of formula (I), this is normally produced as a mixture with the corresponding 13-acyloxy compound of formula (II) and, accordingly, this mixture is preferably subjected, with or without isolation, to hydrolysis to convert it completely to the 13-hydroxy compound of formula (I). The hydrolysis may be carried out by conventional means for the hydrolysis of organic esters and normally it is not necessary to isolate the 13-hydroxy compound of formula (I) prior to hydrolysis, as it remains intact under normal hydrolysis conditions.

The hydrolysis may be effected in a solvent in the presence of either an acid or a base. There is no particular limitation on the acids or bases to be employed and any such compound commonly used for hydrolysis may equally be used in this reaction. By way of example only, suitable acids include such mineral acids as hydrochloric acid, nitric acid and sulfuric acid (preferably hydrochloric acid) and such bases as sodium acetate, potassium acetate, sodium bicarbonate, sodium carbonate and potassium carbonate.

There is no particular limitation on the nature of the solvent to be employed, provided that it does not adversely affect the reaction. Suitable solvents include: alcohols, such as methanol, ethanol or propanol; ethers, such as diethyl ether, dioxane or tetrahydrofuran; water; and mixtures of any two or more thereof. In addition, it is possible to use as the reaction solvent the reaction medium employed for the production of the compounds of formulae (I) and (II), particularly the carboxylic acid of formula (IV).

The hydrolysis reaction will take place over a wide range of temperatures, and accordingly, the reaction temperature is not particularly limited. Normally we prefer to carry out the reaction at a temperature within the range from −10° C. to +100° C., preferably from 0° C. to 50° C. The time required for the reaction may vary widely, depending upon many factors, notably the reaction temperature, but a period of from 30 minutes to 15 hours, more commonly from 1 to 8 hours, will normally suffice.

At the end of the reaction, the desired 13-hydroxy compound of formula (I) may easily be recovered from the reaction mixture by conventional means. For example, one suitable recovery procedure comprises: pouring the reaction mixture into water; filtering off insoluble matter; if necessary, neutralizing the filtrate; extracting the filtrate with a water-immiscible solvent and then drying the extract; and finally removing the solvent to give the desired 13-hydroxy compound of formula (I). this compound may, if desired, be further purified by such conventional techniques as recrystallization or the various chromatography techniques, particularly column chromatography.

Where the 13-acyloxy compound of formula (II) is desired, this may be separated from the reaction mixture in essentially the same way as described above in relation to the 13-hydroxy compound and may be separated from the 13-hydroxy compound by conventional means, particularly column chromatography.

Compounds of formula (V) may be prepared by reacting the 13-hydroxy compound of formula (I) with a carboxylic acid of formula (VI):

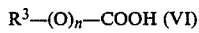

$$R^3-(O)_n-COOH \quad (VI)$$

(in which $R^3$ and n are as defined above) or with a reactive derivative thereof. This reaction constitutes esterification of the hydroxy group at the 13-position of the 13-hydroxy-5-ketomilbemycin compound of formula (I) with the carboxylic acid (VI) or derivative thereof and hence can be effected by any method commonly known for esterification reactions.

Examples of reactive derivatives of the carboxylic acid of formula (VI) include, for example: acid halides, e.g. the acid chloride, acid bromide or acid iodide; acid anhydrides; mixed acid anhydrides; active esters, e.g. the p-nitrobenzyl esters; and active amides, all of which are well-known in the art.

When the carboxylic acid of formula (VI) itself is employed, the reaction is preferably effected in the presence of a dehydrating agent. Such dehydrating agents are well-known for use in esterification reactions and examples include dicyclohexylcarbodiimide, p-toluenesulfonic acid and sulfuric acid, preferably dicyclohexylcarbodiimide. Where dicyclohexylcarbodiimide is employed as the dehydrating agent, we prefer to employ in addition a catalytic amount of pyridine or of 4-pyrrolidinopyridine. Dicyclohexylcarbodiimide is preferably employed in an amount of from 1 to 5 equivalents, more preferably from 1.5 to 4 equivalents, per equivalent of the compound of formula (I).

The reaction is preferably effected in a solvent, the nature of which is not critical, provided that it does not interfere with the reaction. Examples of such solvents include: hydrocarbons, such as hexane, petroleum ether, benzene, toluene or xylene; halogenated hydrocarbons, such as chloroform, methylene chloride or o-chlorobenzene; ethers, such as diethyl ether, tetrahydrofuran, dioxane or ethylene glycol dimethyl ether; and esters, such as methyl acetate or ethyl acetate.

The reaction will take place over a wide range of temperatures, and we generally find it convenient to carry out the reaction at a temperature within the range from 0° to 50° C., more preferably from 0° to 20° C. The time required for the reaction will vary widely, depending upon many factors, but notably the reaction temperature. However, at temperatures within the suggested range, a period of from 30 minutes to 3 hours will normally suffice.

Where an acid halide of the carboxylic acid of formula (VI) is used as the reactive derivative, the reaction is preferably effected in the presence of a base, in order to neutralize the hydrohalic acid produced. Any base commonly used for this purpose may be employed without any particular limitation, but normally an organic base will be used, for example triethylamine, N,N-dimethylaniline, pyridine, 4-dimethylaminopyridine, 1,5-diazobicyclo[4.3.0]nonene-5 or 1,8-diazobicyclo[5.4.0]undecene-7.

The amount of acid halide employed is preferably from 1 to 10 equivalents per equivalent of the 13-hydroxy compound of formula (I), and the base is preferably employed in an amount of from 2 to 5 equivalents per equivalent of the 13-hydroxy compound.

The reaction is preferably effected in the presence of a solvent, and examples of suitable solvents, reaction temperatures and reaction times are as given in relation to the reaction when the carboxylic acid itself is employed.

Reaction conditions wen using other reactive derivatives of the carboxylicd acid of formula (VI), for example the acid anhydrides, mixed acid anhydrides, active esters or active amides, are well-known to those skilled in the art and such reactions may be carried out by conventional means.

At the end of the reaction, the desired compound of formula (V) may be recovered from the reaction mixture by any conventional method, for example as described above in relation to the compounds of formula (I) and may, if desired, be purified by conventional means, including column chromatography.

The compounds of formulae (I) and (V) can exist in the form of α- and β-isomers as a result of the substituent at the 13-position. Depending upon the reaction conditions employed, either of these isomers may be preferentially obtained or there may be obtained a mixture. Where a mixture is obtained, this may be employed as such or the individual isomers may be separated by conventional means. The present invention embraces both of the individual, isolated isomers as well as mixtures thereof.

The invention is further illustrated by the following non-limiting Examples. In these Examples, where a product was purified by column chromatography, it was eluted using a gradient system in which hexane alone was first employed and gradually increasing amounts of ethyl acetate were added.

EXAMPLE 1

13-Hydroxy-5-ketomilbemycin A₄ & 13-formyloxy-5-ketomilbemycin A₄

0.56 g of selenium oxide was added to a solution of 2.0 g of 5-ketomilbemycin A₄ in 25 ml of formic acid, and the mixture was stirred at 40° C., for 2 hours. At the end of this time, a Celite (trade mark) filter aid was added to the reaction liquor and the selenium compound was filtered off. The filtrate was poured into water and extracted with ethyl acetate. The extract was dried over anhydrous magnesium sulfate and then concentrated by evaporation under reduced pressure, to give a crude product containing 13-formyloxy-5-ketomilbemycin $A_4$ and a smaller amount of the 13-hydroxy derivative.

120 ml of methanol, 20 ml of 2N hydrochloric acid and 30 ml of dioxane were added to this crude product, and the mixture was stirred at room temperature for 5 hours. At the end of this time, the reaction mixture was poured into water and extracted with ethyl acetate. The organic extract was dried over anhydrous magnesium sulfate and concentrated by evaporation under reduced pressure to give a residue, which was purified by silica gel column chromatography, affording 1.03 g (yield 50%) of the title compound.

Mass spectrum (m/e): 556 (M+), 538 (M+-18).
Nuclear Magnetic Resonance Spectrum (CDCl$_3$) δ ppm:
  1.59 (3H, singlet);
  1.88 (3H, singlet);
  3.08 (1H, doublet of triplets, J=2.6 & 9.7 Hz);
  3.5–3.65 (2H, multiplet);
  3.74 (1H, doublet, J=10 Hz);
  3.86 (1H, singlet);
  4.0 (1H, singlet);
  4.65–4.85 (2H, multiplet);
  5.25 (1H, triplet, J=8.1 Hz);
  5.35–5.5 (2H, multiplet);
  5.75–5.9 (2H, multiplet);
  6.55 (1H, multiplet).

A separately prepared crude sample containing the 13-formyloxy compound was purified by silica gel column chromatography, to give the pure 13-formyloxy compound.

Mass spectrum (m/e): 584 (M+), 566.
Nuclear Magnetic Resonance Spectrum (CDCl$_3$) δ ppm:
  1.56 (3H, singlet);
  1.90 (3H, singlet);
  3.86 (1H, singlet);
  4.01 (1H, singlet);
  5.06 (1H, doublet, J=10.6 Hz);
  8.09 (1H, singlet).

EXAMPLE 2

13-Hydroxy-5-ketomilbemycins $A_4$ and $A_3$ 2.06 g of a mixture of 5-ketomilbemycins $A_4$ and $A_3$ (molar ratio $A_4$:$A_3$=2.3:1), 0.56 g of selenium dioxide and 15 ml of formic acid were reacted and then the product treated as described in Example 1, to give 0.87 g (yield 41%) of the title compound (molar ratio $A_4$ derivative:$A_3$ derivative=2.3:1).

Mass spectrum (m/e): 556 (M+), 542 (M+).

EXAMPLE 3

13-Hydroxy-5-ketomilbemycin D and 13-Acetoxy-5-ketomilbemycin D 0.22 g of selenium oxide was added to a solution of 0.56 g of 5-ketomilbemycin D in 10 ml of acetic acid, and the mixture was stirred at 40° C. for 1 hour. At the end of this time, a Celite (trade mark) filter aid was added to the reaction liquor and the selenium compound was filtered off. The filtrate was poured into water and extracted with ethyl acetate. The extract was washed with an aqueous solution of sodium bicarbonate, dried over anhydrous magnesium sulfate and concentrated by evaporation under reduced pressure. The residue was purified by silica gel column chromatography to give 0.12 g (yield 21%) of 13-acetoxy-5-ketomilbemycin D from the fractions first eluted, followed by 0.18 g (yield 32%) of 13-hydroxy-5-hydroxy-5-ketomilbemycin D.

13-Acetoxy compound

Infrared Absorption Spectrum (KBr) $\nu_{max}$cm$^{-1}$:
3480, 1740, 1715, 1685, 1460.
Mass spectrum (m/e): 612 (M+), 594 (M+-18).
Nuclear Magnetic Resonance Spectrum (CDCl$_3$) δ ppm:
  1.55 (3H, singlet);
  1.90 (3H, singlet);
  2.05+2.09 (together 3H, each singlet);
  6.57 (1H, multiplet).

13-Hydroxy compound

Infrared Absorption Spectrum (Nujol-trade mark-mull) $\nu_{max}$cm$^{-1}$:
3450, 1735, 1715, 1580.
Mass spectrum (m/e): 570 (M+), 552 (M+-18).
Nuclear Magnetic Resonance Spectrum (CDCl$_3$) δ ppm:
  1.58 (3H, singlet);
  1.89 (3H, multiplet);
  4.6–4.8 (2H, multiplet);
  5.23 (triplet);
  5.3–5.45 (multiplet);
  5.6–5.9 (multiplet);
  6.52 (multiplet);
  6.57 (multiplet).

20 ml of methanol, 5 ml of 2N hydrochloric acid and 10 ml of dioxane were added to 0.10 g of the 13-acetoxy-5-ketomilbemycin D obtained as described above, and the mixture was stirred at 50° C. for 5 hours. At the end of this time, the reaction mixture was treated in the same manner as in the hydrolysis of 13-formyloxy-5-ketomilbemycin described in Example 1, giving a further 0.015 g of 13-hydroxy-5-ketomilbemycin D.

EXAMPLE 4

13-Formyloxy-5-ketomilbemycin D 0.17 g of selenium dioxide was added to a solution of 0.56 g of 5-ketomilbemycin D in 10 ml of formic acid, and the mixture was stirred at 40° C. for 2 hours. At the end of this time, a Celite (trade mark) filter aid was added to the reaction mixture, and the selenium compound was filtered off. The filtrate was poured into water and extracted with ethyl acetate. The extract was concentrated by evaporation under reduced pressure, and the residue was purified by silicaa gel column chromatography to give 0.27 g (yield 44%) of the 13-formyloxy derivative and 0.02 g of the 13-hydroxy derivative.

13-Formyloxy derivative

Infrared Absorption Spectrum (KBr) $\nu_{max}$cm$^{-1}$:
3550, 1730, 1685, 1460.
Mass spectrum (m/e): 598 (M+), 580 (M+-18).
Nuclear Magnetic Resonance Spectrum (CDCl$_3$) δ ppm:
  1.56 (3H, singlet);

1.91 (3H, multiplet);
5.06 (1H, doublet, J=10 Hz);
5.35–5.45 (3H, multiplet);
5.8–5.9 (2H, multiplet);
6.58 (1H, multiplet);
8.09 (1H, multiplet).

25 ml of methanol, 10 ml of 1N hydrochloric acid and 15 ml of dioxane were added to 0.20 g of the 13-formyloxy-5-ketomilbemycin D obtained as described above, and the mixture was stirred at room temperature overnight. The reaction liquor was then poured into water and extracted with ethyl acetate. The extract was concentrated by evaporation under reduced pressure and the residue was purified by silica gel column chromatography to give a further 0.14 g of 13-hydroxy-5-ketomilbemycin D.

EXAMPLE 5

13-(p-Fluorophenoxy)acetoxy-5-ketomilbemycin $A_4$ 23 mg of 1,3-dicyclohexylcarbodiimide, 62 mg of 13-hydroxy-5-ketomilbemycin $A_4$ and a catalytic amount of 4-pyrrolidinopyridine were added, in turn, to a solution of 17 mg of p-fluorophenoxyacetic acid in 15 ml of methylene chloride and the mixture was stirred at room temperature for 30 minutes. At the end of this time, the reaction mixture was filtered and the filtrate was poured into water and then extracted with ethyl acetate. The extract was washed, in turn, with water and with a saturated aqueous solution of sodium chloride, dried over anhydrous magnesium sulfate and then concentrated by evaporation under reduced pressure. The residue was purified by column chromatography through silica gel to give 44 mg (yield 62%) of the title compound.

Infrared Absorption Spectrum (KBr) $\nu_{max}$cm$^{-1}$:
3450 (broad), 1735, 1680, 1505.

Mass spectrum (m/e): 708 (M+), 690.

Nuclear Magnetic Resonance Spectrum (CDCl$_3$) δ ppm:
2.58 (1H, multiplet);
3.05 (1H, doubled triplet, J=3.1 & 9.5 Hz);
3.86 (1H, singlet);
4.01 (1H, singlet);
4.59 (2H, singlet);
5.06 (1H, doublet, J=10.3 Hz);
6.53 (1H, doublet, J=1.5 Hz);
6.8–6.9 (2H, multiplet);
6.93–7.05 (2H, multiplet).

EXAMPLE 6

13-(p-Chlorobenzoyloxy)-5-ketomilbemycin $A_4$

64 μl of pyridine and 102 μl of p-chlorobenzoyl chloride were added to a solution of 56 mg of 13-hydroxy-5-ketomilbemycin $A_4$ in 2 ml of benzene, and then the mixture was stirred at room temperature for 5 hours. At the end of this time, the reaction mixture was poured into water and extracted with ethyl acetate. The extract was dried over anhydrous sodium sulfate and then concentrated by evaporation under reduced pressure. The residue was purified by column chromatography through silica gel to give 37 mg (yield 53%) of the title compound.

Mass spectrum (m/e): 694 (M+), 676.

Nuclear Magnetic Resonance Spectrum (CDCl$_3$) δ ppm:
2.86 (1H, multiplet);
3.18 (1H, doubled triplet, J=3 & 9.5 Hz);
3.67–3.8 (3H, multiplet);
3.98 (1H, singlet);
5.3 (1H, doublet, J=10.6 Hz);
7.5–7.6 (2H, multiplet);
8.05–8.2 (2H, multiplet).

EXAMPLE 7

13-(2-Furoyloxy)-5-ketomilbemycin $A_4$ 336 mg of 13-hydroxy-5-ketomilbemycin $A_4$ and 313 mg of 2-furoyl chloride were reacted in the same manner as described in Example 6 to give 181 mg of the title compound.

Infrared Absorption Spectrum (KBr) $\nu_{max}$cm$^{-1}$:
3450 (borad), 1720, 1680, 1580.

Mass spectrum (m/e): 650 (M+), 632, 538, 520.

Nuclear Magnetic Resonance Spectrum (CDCl$_3$) δ ppm:
5.18 (1H, doublet, J=10.6 Hz);
5.4–5.6 (3H, multiplet);
5.85–5.95 (2H, multiplet);
6.5–6.65 (2H, multiplet);
7.18 (1H, multiplet);
7.58 (1H, multiplet).

EXAMPLE 8

13-(o-Trifluoromethylbenzoyloxy)-5-ketomilbemycin $A_4$ 336 mg of 13-hydroxy-5-ketomilbemycin $A_4$ and 500 mg of (o-trifluoromethyl)benzoyl chloride were reacted in the same manner as described in Example 6 to give 270 mg of the title compound.

Infrared Absorption Spectrum (KBr) $\nu_{max}$cm$^{-1}$:
3450 (broad), 1735, 1680, 1605, 1585.

Mass spectrum (m/e): 710 (M+-18), 610, 520.

Nuclear Magnetic Resonance Spectrum (CDCl$_3$) δ ppm:
5.22 (1H, doublet, J=10.6 Hz);
5.4–5.6 (3H, multiplet);
5.85–5.95 (2H, multiplet);
6.55 (1H, multiplet);
7.55–7.85 (4H, multiplet).

EXAMPLE 9

13-(p-t-Butylbenzoyloxy)-5-ketomilbemycin $A_4$ 336 mg of 13-hydroxy-5-ketomilbemycin $A_4$ and 464 μl of p-t-butylbenzoyl chloride were reacted in the same manner as described in Example 6 to give 197 mg of the title compound.

Infrared Absorption Spectrum (KBr) $\nu_{max}$cm$^{-1}$:
3450 (broad), 1720, 1685, 1610.

Mass spectrum (m/e): 698 (M+-18), 636.

Nuclear Magnetic Resonance Spectrum (CDCl$_3$) δ ppm:
1.34 (9H, singlet);
5.20 (1H, doublet, J=10.3 Hz);
5.4–5.55 (3H, multiplet);
5.8–5.95 (2H, multiplet);
6.55 (1H, multiplet);
7.45–7.55 (2H, multiplet);
7.9–8.1 (2H, multiplet).

EXAMPLE 10

13-Phenylacetyloxy-5-ketomilbemycins $A_4$ and $A_3$ 290 mg of a mixture of 13-hydroxy-5-ketomilbemycins $A_4$ and $A_3$ (molar ratio $A_4:A_3=2.3:1$) and 0.28 ml of phenylacetyl chloride were reacted in the same manner as described in Example 6 to give 262 mg of the title compound (molar ratio $A_4$ derivative:$A_3$ derivative=2.4:1).

Mass spectrum (m/e): 656 ($M^+$-18), 642 ($M^+$-18), 520, 506.

Liquid chromatography [Radialpack NOVA-PAK $C_{18}$, Waters Co., 10% v/v aqueous methanol, 2 ml/min, detected by ultraviolet absorption (254 Lk nm)]: $R_t=4.97$ ($A_3$ derivative, 28.6%), 5.87 ($A_4$ derivative, 68.5%).

EXAMPLE 11

13-(3-Chloropropionyloxy)-5-ketomilbemycins $A_4$ and $A_3$ 200 mg of a mixture of 13-hydroxy-5-ketomilbemycins $A_4$ and $A_3$ (molar ratio $A_4:A_3=2.3:1$) and 0.14 ml of 3-chloropropionyl chloride were reacted in the same manner as described in Example 6 to give 96 mg of the title compound (molar ratio $A_4$ derivative:$A_3$ derivative=2.4:1).

Infrared Absorption Spectrum (CHCl$_3$) $\nu_{max}$cm$^{-1}$: 1730, 1720, 1680.

Mass spectrum (m/e): 646 ($M^+$), 632 ($M^+$), 628, 614.

EXAMPLE 12

13-(2,2,2-Trichloroethoxycarbonyloxy)-5-ketomilbemycins $A_4$ and $A_3$ 496 mg of a mixture of 13-hydroxy-5-ketomilbemycins $A_4$ and $A_3$ (molar ratio $A_4:A_3=2.3:1$) and 0.51 ml of 2,2,2-trichloroethyl chloroformate were reacted in the same manner as described in Example 6, to give 480 mg of the title compound (molar ratio $A_4$ derivative:$A_3$ derivative=2.3:1).

Mass spectrum (m/e): 730 ($M^+$), 716 ($M^+$), 712, 698.

Nuclear Magnetic Resonance Spectrum (CDCl$_3$) δ ppm:
4.68 (1H, doublet, J=12 Hz);
4.76 (2H, singlet);
4.81 (1H, doublet, J=10.6 Hz);
4.83 (1H, doublet, J=12 Hz).

EXAMPLE 13

13-Methoxycarbonyloxy-5-ketomilbemycins $A_4$ and $A_3$ 500 mg of a mixture of 13-hydroxy-5-ketomilbemycins $A_4$ and $A_3$ (molar ratio $A_4:A_3=2.3:1$) and 0.45 ml of methyl chloroformate were reacted in the same manner as described in Example 6, to give 380 mg of the title compound (molar ratio $A_4$ derivative:$A_3$ derivative=2.3:1).

Mass spectrum (m/e): 614 ($M^+$), 600 ($M^+$), 598, 584.

Nuclear Magnetic Resonance Spectrum (CDCl$_3$) δ ppm:
3.80 (3H, singlet);
4.65–4.85 (3H, multiplet).

EXAMPLE 14

13-Ethoxycarbonyloxy-5-ketomilbemycin D 228 mg of 13-hydroxy-5-ketomilbemycin D and 0.16 ml of ethyl chloroformate were reacted in the same manner as described in Example 6, to give 205 mg of the title compound.

Infrared Absorption Spectrum (KBr) $\nu_{max}$cm$^{-1}$: 3480, 1745, 1685.

Mass spectrum (m/e): 642 ($M^+$), 624, 606, 591, 552, 534.

Nuclear Magnetic Resonance Spectrum (CDCl$_3$) δ ppm:
4.15–4.25 (2H, multiplet);
4.7–4.8 (3H, multiplet).

EXAMPLE 15

13-Ethoxycarbonyloxy-5-ketomilbemycin $A_4$ 285 mg of 13-hydroxy-5-ketomilbemycin $A_4$ and 0.20 ml of ethyl chloroformate were reacted in the same manner as described in Example 6, to give 301 mg of the title compound.

Infrared Absorption Spectrum (KBr) $\nu_{max}$cm$^{-1}$: 3480, 1745.

Mass spectrum (m/e): 628 ($M^+$), 610.

EXAMPLE 16

13-(2,2-Dimethyl-1,3-dioxolan-4-ylmethoxycarbonyloxy)-5-ketomilbemycins $A_4$ and $A_3$ 500 mg of a mixture of 13-hydroxy-5-ketomilbemycins $A_4$ and $A_3$ (molar ratio $A_4:A_3=2.3:1$) and 1.2 g of 2,2-dimethyl-1,3-dioxolan-4-ylmethyl chloroformate were reacted in the same manner as described in Example 6, to give 550 mg of the title compound (molar ratio $A_4$ derivative:$A_3$ derivative=2.3:1).

Infrared Absorption Sepctrum (CDCl$_3$) $\nu_{max}$cm$^{-1}$: 1745, 1680.

Mass spectrum (m/e): 714 ($M^+$), 700 ($M^+$), 696, 682.

Nuclear Magnetic Resonance Spectrum (CDCl$_3$) δ ppm:
1.36 (3H, singlet);
1.43 (3H, singlet);
2.6 (1H, multiplet);
3.05 (1H, doubled triplet, J=2.5 & 9.5 Hz);
3.55–3.7 (2H, multiplet);
3.8 (1H, multiplet);
4.05–4.2 (3H, multiplet);
4.32 (1H, multiplet);
4.75 (3H, multiplet).

EXAMPLE 17

13-Benzyloxycarbonyloxy-5-ketomilbemycins $A_4$ and $A_3$ 256 mg of a mixture of 13-hydroxy-5-ketomilbemycins $A_4$ and $A_3$ (molar ratio $A_4:A_3=2.3:1$) and 654 mg of benzyl chloroformate were reacted in the same manner as described in Example 6, to give 233 mg of the title compound (molar ratio $A_4$ derivative:$A_3$ derivative=2.3:1).

Mass spectrum (m/e): 690 ($M^+$) and 676 ($M^+$).

Nuclear Magnetic Resonance Spectrum (CDCl$_3$) δ ppm:
4.7–4.85 (3H, multiplet);
5.11 (1H, doublet, J=12.1 Hz);
5.18 (1H, doublet, J=12.1 Hz);
7.38 (5H, multiplet).

EXAMPLE 18

13-(2-Methoxyethoxycarbonyloxy)-5-ketomilbemycin A$_4$ 278 mg of 13-hhdroxy-5-ketomilbemycin A$_4$ and 0.23 ml of 2-methoxyethyl chloroformate were reacted in the same manner as described in Example 6, to give 182 mg of the title compound.

Infrared Absorption Spectrum (KBr) $\nu_{max}$cm$^{-1}$: 3560, 1745, 1680.

Mass spectrum (m/e): 658 (M$^+$), 640, 538.

Nuclear Magnetic Resonance Spectrum (CDCl$_3$) δ ppm:
3.39 (3H, singlet);
3.5–3.7 (4H, multiplet);
4.2–4.35 (2H, multiplet);
4.65–4.85 (3H, multiplet).

EXAMPLE 19

13-Pivaloyloxy-5-ketomilbemycin A$_4$

A mixture of 300 mg of 13-hydroxy-5-ketomilbemycin A$_4$, 0.86 ml of pyridine and 1.32 ml of pivaloyl chloride was reacted at 80° C. for 2 hours and then the product was treated as described in Example 6, to give 220 mg of the title compound.

Mass spectrum (m/e): 640 (M$^+$), 622, 582, 538, 520.

EXAMPLE 20

13-(p-Bromobenzoyloxy)-5-ketomilbemycin A$_4$ 420 mg of 13-hydroxy-5-ketomilbemycin A$_4$ and 0.50 g of p-bromobenzoyl chloride were reacted as described in Example 6, to give 250 mg of the title compound.

Mass spectrum (m/e): 738 (M$^+$), 720, 538, 520.

Nuclear Magnetic Resonance Spectrum (CDCl$_3$) δ ppm:
5.20 (1H, doublet, J=10.6 Hz);
7.59 (2H, doublet, J=8.2 Hz);
7.89 (2H, doublet, J=8.2 Hz).

EXAMPLE 21

13-Trifluoromethylbenzoyloxy)-5-ketomilbemycin A$_4$ and A$_3$ 556 mg of a mixture of 13-hydroxy-5-ketomilbemycins A$_4$ and A$_3$ (molar ratio A$_4$:A$_3$=2.3:1) and 0.59 ml of p-trifluoromethylbenozyl chloride were reacted as described in Example 6, to give 484 mg of the title compound (molar ratio A$_4$ derivative:A$_3$ derivative=2.5:1).

Mass spectrum (m/e): 728 (M$^+$), 714 (M$^+$), 710, 696.

Nuclear Magnetic Resonance Spectrum (CDCl$_3$) δ ppm:
5.23 (1H, doublet, J=10.3 Hz);
8.15 (2H, doublet, J=8.6 Hz);
8.21 (2H, doublet, J=8.6 Hz).

EXAMPLE 22

13-Trichloroacetoxy-5-ketomilbemycin A$_4$ 200 mg of 13-hydroxy-5-ketomilbemycin A$_4$ and 0.10 ml of trichloroacetyl chloride were reacted as described in Example 6, to give 201 mg of the title compound.

Mass spectrum (m/e): 715 (M$^+$, calculating Cl as 35), 697.

Nuclear Magnetic Resonance Spectrum (CDCl$_3$) δ ppm:
4.99 (1H, doublet, J=10.6 Hz).

EXAMPLE 23

13-Iodoacetoxy-5-ketomilbemycin A$_4$ 268 mg of iodoacetic acid and 200 mg of 13-hydroxy-5-ketomilbemycin A$_4$ were reacted as described in Example 6, to give 114 mg of the title compound.

Mass spectrum (m/e): 724 (M$^+$), 706.

Nuclear Magnetic Resonance Spectrum (CDCl$_3$) δ ppm:
3.69 (2H, singlet);
4.94 (1H, doublet, J=10.7 Hz).

EXAMPLE 24

13-Crotonoyloxy-5-ketomilbemycin A$_4$ and A$_3$ 256 mg of a mixture of 13-hydroxy-5-ketomilbemycins A$_4$ and A$_3$ (molar ratio A$_4$:A$_3$=2.3:1) and 0.11 ml of crotonoyl chloride were reacted as described in Example 6, to give 82 mg of the title compound (molar ratio A$_4$ derivative:A$_3$ derivative=2.5:1).

Mass spectrum (m/e): 624 (M$^+$), 606.

Nuclear Magnetic Resonance Spectrum (CDCl$_3$) δ ppm:
5.01 (1H, doublet, J=10.6 Hz).

We claim:

1. A compound or mixture of compounds of formula (V):

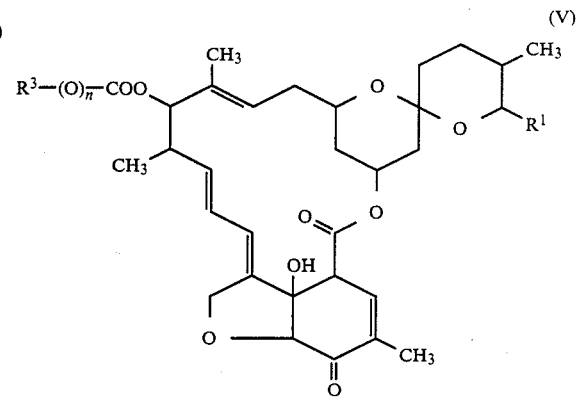

wherein:
R$^1$ represents a methyl, ethyl, isopropyl or sec-butyl group;
n is 0 or 1; and
R$^3$ represents a hydrogen atom, a C$_1$–C$_{18}$ alkyl group, a C$_3$–C$_{10}$ cycloalkyl group, a C$_7$–C$_9$ aralkyl group, a C$_2$–C$_6$ alkenyl group, a C$_2$–C$_6$ alkynyl group, a C$_5$–C$_{10}$ cycloalkenyl group or a C$_6$–C$_{10}$ carbocyclic aryl group or said alkyl, alkenyl or alkynyl group having one, two or three substituents selected from the group consisting of substituents (a); or said cycloalkyl, cycloalkenyl, aralkyl or aryl having one two or three substituents selected from the group consisting of substituents (a) and (b):
substituents (a): C$_1$–C$_6$ alkoxy groups, C$_2$–C$_7$ alkoxycarbonyl groups, halogen atoms, hydroxy groups, carboxy groups, amino groups, C$_1$–C$_6$ alkylamino groups, dialkylamino groups where each alkyl part is C$_1$–C$_6$, carboxylic acylamino groups, cyano groups, carbamoyl groups, alkylcarbamoyl groups where the alkyl part is C$_1$–C$_6$, dialkylcarbamoyl groups where each alkyl part is C$_1$–C$_6$, mercapto groups, C$_1$–C$_6$ alkylthio groups, $C_1$–$C_6$ alkylsulfinyl groups, $C_1$–$C_6$ alkylsulfonyl groups, nitro groups, phenoxy groups, phenoxy groups having from 1 to 5 halogen substituents and substituents (b): $C_1$–$C_6$ alkyl groups, $C_2$–$C_6$ alkenyl groups, $C_2$–$C_6$ alkenyl groups having at least one halogen substituent, alkoxyalkyl groups where both the alkoxy and the alkyl parts have one to six carbon atoms having at least one halogen substituent.

2. A compound as claimed in claim 1, wherein $R^3$ represents the methyl, ethyl, isopropyl, butyl, t-butyl, pentyl, octyl, trifluoromethyl, 2-chloroethyl, 2,2,2-trichloroethyl, 2,2,2-trifluoroethyl, 1-chloropropyl, methoxymethyl, 2-methoxyethyl, 2-ethoxyethyl, phenoxymethyl, 4-fluorophenoxymethyl, 2-hydroxyethyl, 2-mercaptoethyl, 2-carboxyethyl, cyclopropyl, 2-(2,2-dichlorovinyl)-3,3-dimethylcyclopropyl, cyclobutyl, 2,2-dichlorovinyl, 1,2,2-trichlorovinyl, 2,2-difulorovinyl, 1-propenyl, allyl, isopropenyl, 1-butenyl, 2-butenyl, 2-methylallyl, ethynyl, 2-propynyl, 1-cyclohexenyl, benzyl, phenyl, o-chlorophenyl, m-chlorophenyl, p-chlorophenyl, o-fluorophenyl, m-fluorophenyl, p-fluorophenyl, o-bromophenyl, m-bromophenyl, p-bromophenyl, p-methoxyphenyl, p-nitrophenyl, p-t-butylphenyl, o-trifluoromethylphenyl, m-trifluoromethylphenyl.

3. A compound as claimed in claim 1, wherein $R^1$ represents a methyl, ethyl or isopropyl group.

4. A compound as claimed in claim 1, wherein said compound of formula (V) is a compound where $R^1$ represents a methyl or ethyl group or is a mixture of such compounds.

5. A compound as claimed in claim 1, wherein $R^1$ represents an isopropyl group.

6. A compound as claimed in claim 1, wherein $R^3$ represents a hydrogen atom.

7. A compound as claimed in claim 1, wherein $R^3$ represents a methyl group.

8. 13-Formuloxy-5-ketomilbemycin $A_4$ of formula of claim 1.

9. 13-Acetoxy-5-ketomilbemycin D of formula of claim 1.

10. 13-Formyloxy-5-ketomilbemycin D of formula of claim 1.

11. 13-(p-Fluorophenoxy)acetoxy-5-ketomilbemycin $A_4$ of formula of claim 1.

12. 13-(p-Chlorobenzoyloxy)-5-ketomilbemycin $A_4$ of formula of claim 1.

13. 13-(o-Trifluoromethylbenzoyloxy)-5-ketomilbemycin $A_4$ of formula of claim 1.

14. 13-(p-t-Butylbenzoyloxy)-5-ketomilbemycin $A_4$ of formula of claim 1.

15. A mixture of 13-phenylacetoxy-5-ketomilbemycins $A_4$ and $A_3$ of formula of claim 1.

16. A mixture of 13-(3-chloropropionyloxy)-5-ketomilbemycins $A_4$ and $A_3$ of formula of claim 1.

17. A mixture of 13-(2,2,2-trichloroethoxycarbonyloxy)-5-ketomilbemycins $A_4$ and $A_3$ of formula of claim 1.

18. A mixture of 13-methoxycarbonyloxy-5-ketomilbemycins $A_4$ and $A_3$ of formula of claim 1.

19. 13-Ethoxycarbonyloxy-5-ketomilbemycin D of formula of claim 1.

20. 13-Ethoxycarbonyloxy-5-ketomilbemycin $A_4$ of formula of claim 1.

21. A mixture of 13-benzyloxycarbonyloxy-5-ketomilbemycins $A_4$ and $A_3$ of formula of claim 1.

22. A mixture of 13-(2-methoxyethoxycarbonyloxy)-5-ketomilbemycins $A_4$ and $A_3$ of formula of claim 1.

23. 13-Pivaloyloxy-5-ketomilbemycin $A_4$ of formula of claim 1.

24. 13-(p-Bromobenzoyloxy)-5-ketomilbeycin $A_4$ of formula of claim 1.

25. A mixture of 13-(p-trifluoromethylbenozyloxy)-5-ketomilbemycins $A_4$ and $A_3$ of formula of claim 1.

26. 13-Trichloroacetoxy-5-ketomilbemycin $A_4$ of formula of claim 1.

27. 13-Iodoacetoxy-5-ketomilbemycin $A_4$ of formula of claim 1.

28. A mixture of 13-crotonoyloxy-5-ketomilbemycins $A_4$ and $A_3$ of formula of claim 1.

29. The compound or mixture of compounds of claim 1, wherein said alkyl, alkenyl or alkynyl group has a second substituent selected from the group consisting of substituents (a).

30. The compound or mixture of compounds of claim 13, wherein said alkyl, alkenyl or alkynyl group has a third substituent selected from the group consisting of substituents (a).

* * * * *